United States Patent [19]

Tung et al.

[11] 4,062,949

[45] Dec. 13, 1977

[54] ABRIN COMPOSITION OF REDUCED TOXICITY

[75] Inventors: Ta-Cheng Tung; Jung-Yaw Lin, both of Taipei, China /Taiwan

[73] Assignee: Eisai Co., Ltd., Japan

[21] Appl. No.: 570,372

[22] Filed: Apr. 22, 1975

[30] Foreign Application Priority Data

Apr. 30, 1974 Japan .................................. 49-47593

[51] Int. Cl.$^2$ ....................... A61K 31/70; A61K 35/78

[52] U.S. Cl. ..................................... 424/180; 424/195

[58] Field of Search ................................ 424/195, 180

[56] References Cited

PUBLICATIONS

Dyer, An Index of Tumor Chemotherapy, N.I.H., Mar. 1949, pp. 10–12, 145, 146 and 175.

*Primary Examiner*—Jerome D. Goldberg

*Attorney, Agent, or Firm*—Wenderoth, Lind & Ponack

[57] ABSTRACT

A pharmaceutical composition comprising abrin and nucleic acid wherein the ratio of abrin to nucleic acid is about 1:40 by weight is provided. The composition has less toxicity than abrin alone.

1 Claim, No Drawings

ABRIN COMPOSITION OF REDUCED TOXICITY

The present invention relates to new anti-cancer pharmaceutical compositions. More particularly, the present invention relates to a new pharmaceutical composition comprising abrin and nucleic acid. The present invention also relates to a method for treating cancers which comprises administering a pharmaceutical composition comprising abrin and nucleic acid.

In accordance with the present invention, therefore, there are provided a new pharmaceutical composition comprising abrin and nucleic acid as well as method for treatment of cancer therewith.

Abrin used in the present invention is a toxic protein (toxalbumin) having molecular weight of about 65,000 which is naturally present in the seeds of jequirity, *Abrus Precatorius*, in the tropics and the subtropical zones.

Although various procedures for isolating abrin from *Abrus precatorius* have already been known to the art, a preferable procedure for the purpose of obtaining highly purified abrin is reported by J. Y. Lin et. al. "The journal of the Formosan Medical Association, 68, 518–521 (1969)". The detail of said procedure is following:

100 G. of kernels of *Abrus precatorius* is soaked in 500 ml. of 5% acetic acid at a temperature of 4° C. overnight and then homogenized in a Waring blender. The homogenate is centrifuged in 250 ml. bottles in an International centrifuge for 20 minutes at 5,000 g and the residue is discarded. To the supernatant, solid ammonium sulfate is added slowly with stirring to 45% saturation.

The precipitate in which very little toxic protein has been detected is filtered off. To the supernatant is added solid ammonium sulfate to 100% saturation. The resulting precipitate is dissolved in distilled water and further purified by heating the toxic protein in a water bath at 60° C. for 30 minutes. The resulting precipitate of the protein is centrifuged off and the supernatant is dialyzed against distilled water at 4° C for 24 hours with several changes of distilled water.

During dialysis, some precipitate of protein occurred, which is then removed by centrifugation. The supernatant is purified on a DEAE-Sephadex A-50 (sold by Pharmacia A. B., Uppsala, Sweden) column (2 × 50 cm) which is previously equilibrated with 0.005 M sodium acetate. Samples are collected in a Gilson fraction collector.

The fractions of the protein peak are pooled and concentrated to about 20 mg. of protein per ml. by evaporation. As water evaporated from the surface of the bag, the crystals appear as indicated by the shimmering of the solution. For recrystallization, the crystals are dissolved in distilled water by adding a few drops of 0.1 N acetic acid. Then, it is dialyzed against distilled water, and crystals reappeared after several changes of distilled water are filtered off. There are thus obtained 120 mg. of pure abrin as the fine rod-shape crystals.

The product shows a single band by the disc gel electrophoresis. The absorbance (280 nm.) of the product in a 1-cm. cell is found to be 12.4. The ratio of optical absorption at 280 and 260 nm. is 1.95. The product is shown to be free from protease activity and hemagglutinating activity.

Nucleic acid to be used in the present invention includes both RNA (Ribonucleic acid) and DNA (Deoxyribonucleic acid).

Any of the commercially available RNA and DNA can be used in the present invention. Examples of such RNA are those which are derived from, for example, baker's yeast, brewer's yeast, Torula yeast, *Escherichia coli*, beef liver, and the like. Examples of such DNA are those which are derived from, for example, calf thymus, salmon sperm, herring sperm, *Clostridium perfringens*, and the like.

The present inventors have previously found and reported that administration of abrin may be used for treatment of cancers, such as for example uterine and ovarin cancers; see, J. Formosan Med. Assoc., 70, No. 10, pp. 569–578 (1971). There are, however, some drawbacks in the administration of abrin. Thus, abrin is a remarkably toxic substance having $LD_{50} = 0.02$ mg per Kg. body weight (in mice, intraperitoneally). Because of its highly toxic property, administering procedures are limited to a topical application in a form of semi-solid preparation, intratumorous injection, intraperitoneal administration, retroperitoneal administration and intra-artereal infusion. And, the intravenous administration of abrin could not be applied, since it might result in death. It was further observed that when abrin is administered intraperitoneally or intratumorously, some side effects such as dizziness, transient fever and a trace of proteinuria may be often encountered.

According to the present invention, there is provided new pharmaceutical composition comprising abrin together with nucleic acid, which possesses substantially the same anti-tumor activity as that of abrin per se, while the toxicity and side-effects of which are remarkably diminished.

Ratio of nucleic acid to abrin in the composition of the present invention is about 0.3 by weight or more, and preferably about 10 to 50.

Various pharmaceutical preparations can be advantageously prepared in accordance with the known procedures to those skilled in the art, which contain abrin and nucleic acid together with a conventional liquid, solid and/or semi-solid carriers. Suitable preparations containing abrin and nucleic acid include injectable solution, injectable solid preparation for extemporaneous dilution, and semi-solid preparations for topical application, for example, ointment, suppository, and the like. Such preparations may further contain other pharmaceutically active materials such as local anesthetics, agents for accelerating diffusion of the active ingredient into the tissue suffering from cancers, and/or other anti-cancer agents, etc.

The semi-solid preparation, for example, ointment may be formulated employing conventional ointment bases such as for example white petrolatum, liquid petrolatum, lanolin, vegetable oils, waxes, polyethylene glycols, etc. or mixture thereof. To enhance the diffusion of the preparations in the tissue, these preparations may additionally be contain proper amount of hyaluronidase.

In the case of the injectable solid preparation for extemporaneous dilution, there may be used suitable diluents such as normal saline, in order to dilute said preparation in proper concentration of abrin.

In the production of an aqueous injectable preparation and the dissolution step prior to the use of injectable solid preparations for extemporaneous dilution, it is necessary to adjust a pH value to approximately 7 or above, since abrin forms a precipitate with nucleic acid in an aqueous medium having a pH value less than about 6.

Injectable preparations according to the present invention can be administered intratumorously, intraperitoneally, retroperitoneally or intra-arterially, same as in the cases of administration of abrin per se. Further, the preparations can also be administered intra venously, because of its relatively low toxicity as mentioned above.

The dose of the pharmaceutical preparations according to the present invention may be varied depending upon the administration methods, or the kind or severity of cancer. Recommendable dose of injectable preparation ranges from about 0.5 μg. to about 30 μg. per day as abrin, in the case of intratumorous administration; from about 50 μg to about 600 μg. per day, in the case of intraperitoneal, retroperitoneal and intra-artereal administrations; and from about 5 μg. to about 40 μg per day, in the case of intravenous administration.

The followings illustrate toxicity test, pharmacological test experiments, by using compositions comprising abrin and nucleic acid according to the present invention.

TOXICITY TEST

By using the injectable preparation containing abrin and ribonucleic acid in a ratio of 1 : 40 by weight produced in accordance with Example 1 hereinaftermentioned, the respective injections were applied to the vein of front leg of the dog, the marginal ear vein of rabbit, and femoral vein of the rat, in order to obtain the $LD_{50}$ values. The results are shown in the following Table 1.

Table 1

| Animal | Dose (μg/Kg, as abrin) of abrin-ribonucleic acid containing preparation | Dose (μg/Kg) of abrin along |
| --- | --- | --- |
| Dog | 18 | 7.5 |
| Rabbit | 16 | 7.5 |
| Rat | 14 | 7.5 |

When the same injectable preparation was gradually administered intravaneously to the dog over 12 hours, the $LD_{50}$ value was 30 μg/Kg as abrin.

From the data of the above Table 1, it is appreciated that the toxicity of the composition comprising abrin and ribonucleic acid of the present invention is about half or less, as compared with that of abrin alone.

The reason why the toxicity of the abrin-nucleic acid containing composition according to the present invention is much lowered than that of abrin per se may be explained as follows; the active sites of abrin is masked by nucleic acid, therefore the toxic activity of abrin against animal cells is remarkably diminished. It is presumed that, after the administration of the present composition, abrin is gradually freed from the complex and exert the anti-tumor activity.

PHARMACOLOGICAL TEST

The pharmacological effect of the abrin-ribonucleic acid (1 : 40) containing composition was confirmed according to the method reported by E. N. Sassenrath (Ann. N. Y. Acad. Sci., 76, 1958); thus, animals in each group consisting of from 7 to 10 mice (average body weight, ca. 20 g ± 1g) were transplanted with $1 \times 10^7$ tumor cells intraperitoneally and the solution containing abrin-ribonucleic acid (1 : 40) in 0.9% aqueous NaCl were administered intraperitoneally to mice in various dose levels once a day for 5 days, starting 24 hours after transplantation of tumor cells. Amount of ascites accumulated was measured using graduated cylinder and packed cell volume was determined in capillary tube by microhematocrit centrifugation. Total packed cell volume (TPCV) was calculated by multiplication of these two values. Anti-tumor activity was expressed as percentage of the average total packed cell volume of the treated group (T) to that of the control (C) on the 7th day after transplantation. The ratio of daily doses of the abrin-ribonucleic acid containing composition to the percentage of the tumor growth (T/C %) in shown in Table 2

Table 2

| Daily dose (μg/Kg, as abrin) of Abrin-ribonucleic acid containing composition | Percentage of tumor growth (T/C %) |
| --- | --- |
| 2.50 | 1.9 |
| 1.25 | 1.4 |
| 0.63 | 11.6 |
| 0.31 | 90.2 |

The maximum inhibitory effect (T/C % = 1.4) was obtained by the five consecutive administrations of the composition in an amount of 1.25 μg. (as abrin), and $ED_{90}$ (T/C % = 10) was estimated approximately 0.63 μg./Kg.

The following Examples illustrate the invention of the present application.

EXAMPLE 1

Solution "A" is prepared by dissolving 10 mg. of crystalline abrin in 1 ml. of 0.01 N acetic acid, adding thereto 0.01 M phosphate buffered physiological saline (pH 4), to make its total volume to 40 ml., and filtering the same through Milliporefilter (Trade Mark).

Solution "B" is prepared by dissolving 100 mg. of purified yeast RNA (Type XI; Sigma Chem. Co., Ltd., St. Louis, Mo., U.S.A.) in 10 ml. of 0.01 M phosphate buffered physiological saline (pH 7.4), and filtering the solution through Milliporefilter.

Equivalent volumes of each of the Solution "A" and the Solution "B" are mixed each other. Each 0.4 ml. of the resulting solution is filled into ampoules which are in turn sealed. Respective ampoules contain 50 μg of abrin and 2 mg of RNA (a ratio of abrin : ribonucleic acid = 1 : 40).

The above whole procedures are carried out at a temperature of 4° C. under the sterilized conditions. The resulting ampoules are preserved at a temperature of 4° C.

EXAMPLE 2

10 Mg. of the Solution "A" in the preceding Example 1and 7.5 ml. of the Solution "B" in the Example 1 are mixed each other. Physiological saline is added to the mixture to make its total volume to 20 ml. Each 0.4 ml. of the resulting solution is filled into ampoules which are in turn sealed. There are thus obtained injectable ampoules which contain 50 μg of abrin and 1.5 mg of ribonucleic acid (a ratio of abrin : ribonucleic acid = 1 : 30).

EXAMPLE 3

10 Ml. of the Solution "A" and 0.75 ml. of the Solution "B", the respective Solutions being previously prepared in the Example 1, are mixed each other. Physiological saline is added to the mixture to make its total volume to 20 ml. Each 0.4 ml. of the resulting solution is filled into ampoules which are in turn sealed. There are thus obtained injectable ampoules, each of which contains 50 μg of abrin and 0.15 mg. of ribonucleic acid (a ratio of abrin : ribonucleic acid = 1 : 3).

EXAMPLE 4

Solution "C" is prepared by dissolving 12.5 mg. of purified calf thymus DNA (Manufactured by Washington Biochemical Corp. Freechold. New Jersey, U.S.A.) into 10 ml. of 0.01 M phosphate buffered physiological saline (pH 7.4), and filtering the same through Milliporefilter.

The Solution "C" is mixed with the Solution "A" which was prepared in the Example 1 in a ratio of the respective equivalent volumes. Each 0.4 ml. of the resulting solution is filled into ampoules which are in turn sealed. There are thus obtained injectable ampoules, each of which contains 50 μg of abrin and 250 μg of DNA (a ratio of abrin : deoxyribonucleic acid = 1 : 5).

EXAMPLE 5

10 Mg. of the Solution "A" prepared in the Example 1 and 0.5 ml. of the Solution "C" prepared in the Example 4 are mixed each other. To the resulting mixture there is added physiological saline to make its total volume to 20 ml. Each 0.4 ml. of the resulting solution is filled into ampoules which are in turn sealed. There are thus obtained injectable ampoules, each of which contains 50 μg of abrin and 15 μg of deoxyribonucleic acid (a ratio of abrin : deoxyribonucleic acid = 1 : 0.3).

EXAMPLE 6

Solution "D" is prepared by dissolving 10 mg. of crystalline abrin into 10 ml. of 0.01 N acetic acid. To the Solution D there are successively added 20 ml. of purified water and 10 ml. of 0.01 N ammonia solution. The mixture is then filtered through Milliporefilter to obtain the Solution "D".

Solution "E" is prepared by dissolving 100 mg. of purified yeast RNA (which is sample as used in the Example 1) and 100 mg of alanine into 10 ml. of purified water, and filtering the same through Milliporefilter.

Equivalent amounts of each of the Solution "D" and the Solution "E" are mixed each other. Each 0.4 ml. of the resulting solution is filled into vials, which are in turn freeze-dried in accordance with the conventional procedures, and sealed in vacuo.

The products are used, for example, by dissolving them into physiological saline, 5% glucose solution, purified water, and the like.

EXAMPLE 7

100 Mg. of crystalline abrin and 300 mg. of yeast ribonucleic acid are dissolved into a small amount of 0.01 N acetic acid. To the solution, there is added phosphate buffer of pH 4 to make its total volume to 10 ml. To the mixture, there is added 2000 units of Hyaluronidase which is previously dissolving it into 4 ml. of physiological saline. To the resulting solution, there are added 10 ml. of polyethylene glycol 300, and mixed with each other. The mixture is further admixed with 150 g. of vehicle which consists of white petrolatum and liquid petrolatum, and the resulting mixture is blended to be homogeneous. There is thus obtained an ointment which contains abrin and ribonucleic acid in a ratio of 1 : 3.

The resulting ointment is usually employed in an amount of about 1 – 10 g. depending upon the size of the tumor or crater.

What is claimed is:

1. An abrin composition of reduced toxicity comprising abrin and nucleic acid, wherein the ratio of abrin to ribonucleic acid is about 1:40 by weight.

* * * * *